United States Patent [19]

Baker

[11] 4,260,899
[45] Apr. 7, 1981

[54] WIDE WEB LASER SCANNER FLAW DETECTION METHOD AND APPARATUS

[75] Inventor: Cole H. Baker, Westport, Conn.

[73] Assignee: Intec Corporation, Trumbull, Conn.

[21] Appl. No.: 48,623

[22] Filed: Jun. 14, 1979

[51] Int. Cl.³ ............................................. G01N 21/88
[52] U.S. Cl. ....................................... 250/563; 356/431
[58] Field of Search ............... 250/562, 563, 571, 572, 250/234, 235, 236; 356/429, 430, 431, 445

[56] References Cited

U.S. PATENT DOCUMENTS

| | | | |
|---|---|---|---|
| 2,803,755 | 8/1957 | Milford | 250/563 |
| 3,866,054 | 2/1975 | Wolf | 250/562 |
| 4,013,367 | 3/1977 | Nagao et al. | 356/431 |

*Primary Examiner*—David C. Nelms
*Attorney, Agent, or Firm*—Parmelee, Johnson, Bollinger & Bramblett

[57] ABSTRACT

A wide web laser scanner flaw detection method and apparatus are provided for rapid and accurate inspection of wide web materials. A plurality of laser sources are scanned by a plurality of aligned synchronized rotary scanners which repetitively scan the sources in sequence on a predetermined scan path over the material being examined with each laser scanning only a portion of the scan line. The rotary scanners are selectively blanked in sequence such that only one rotary scanner is scanning a single laser beam on only a portion of a line scan on the material in any given time interval and the blanking means are staggered such that one complete line scan is formed across the material by consecutive sequential alternating scans of each of the laser sources by each of the rotary scanners. The wide web is moved in a direction transversely with respect to the direction of the scan line for providing a raster type scan pattern along the wide web of material being inspected. Receiver means having detector means therein are positioned for receiving radiation applied by the laser beams from the material being inspected with the detector means generating signals in response to the intensity of the radiation received from the material being inspected by the laser beams. A single electronic processing console is provided having the detector signals applied thereto for processing the signals to detect and locate flaws in the material being inspected.

7 Claims, 4 Drawing Figures

4,260,899

WIDE WEB LASER SCANNER FLAW DETECTION METHOD AND APPARATUS

BACKGROUND OF THE INVENTION

This invention relates to a laser scanner flaw detection systems, and more particularly to a method and apparatus for the inspection of wide web materials by inspecting such materials using a plurality of laser beams which are sequentially scanned over the material using a plurality of aligned synchronized rotary scanners.

In U.S. Pat. No. 3,980,891 entitled "Method and Apparatus for a Rotary Scanner Flaw Detection System", which is assigned to the assignee of the present invention, flaws are detected in the material being examined by repetitively scanning a suitable source of radiation, such as a laser beam, across the surface of the material. The laser beam is directed at a multifaceted rotating mirrored reflector drum which scans the material with a highly collimated scanning radiation beam. The laser light is reflected, transmitted or scattered from the material depending upon the characteristics of the material, which light is collected by a receiver having a suitable detector such as a photomultiplier tube. At any given instant of time during the scan, the photomultiplier output varies with the reflectivity, transmissivity or scattering properties of the spot of radiation on the material upon which the laser beam is impinging, and accordingly deviations from characteristic variations provide a means for indicating material flaws. One form of receiver which may be utilized in this system is shown and described in U.S. Pat. No. 3,900,265 entitled "Laser Scanner Flaw Detection System" which is assigned to the assignee of the present invention.

Another rotary scanner flaw detection system is shown and described in U.S. Pat. No. 3,866,054 entitled "Defect Size Discriminator Circuit for Web Inspection System" in which the receiver comprises a radiation conducting rod which conveys transmitted or reflected radiation from the beam to a photomultiplier tube positioned on the end of the rod. A diffusing strip is positioned in the rod so that when radiation is applied thereto from the material being inspected the radiation is dispersed within the rod causing internal reflection therein thereby transmitting the radiation through the rod to the photomultiplier tube positioned on the end thereof. After signals have been generated in accordance with the intensity of the radiation applied thereto from the material being examined, the signals are processed in an electronic processing circuitry to identify flaws in the material.

The electronic processing circuitry for laser inspection systems have become very sophisticated providing a variety of information about the nature and locations of detected flaws. Accordingly, the electronic processing circuitry will normally be the most expensive part of the system.

In order for the systems to function properly the laser beam must be scanned across the full width of the web of the material being inspected. Accordingly, as the web width increases the height of the scanner above the web increases in order to provide a complete scan across the web. Also as the distance between the web and the scanner increases, the spot size of the laser beam increases thereby reducing system resolution. For example, the normal distance between the scanner and the material being examined for webs up to 120" would be approximately 10'. In order to cover a web of up to 240" with the same scanner, it would have to be elevated in an additional 10' above the web which would double the spot size. Elevating the scanner to such a height may also not be feasible because the facility where the web is produced may not accommodate such a separation simply because enough space is not available or machinery or other super structure near the ceiling would interfere with the positioning or the scanning operation. Furthermore, the heat which is generated in the processing plant, for example, a paper mill would be intense near the ceiling and interfere with the proper functioning of the laser scanner. Alignment problems between the scanner and the receiver also become a problem at such distances.

Furthermore, if reduced spot size and better resolution are required even for narrower webs, such spot size and resolution would be limited by the distance which the scanner must be placed from the web in order to completely cover it with a scan.

SUMMARY OF THE INVENTION

Accordingly, it is an object of this invention to provide a new and novel laser scanner flaw detection systems for inspection of wide web materials.

A further object of this invention is to provide a new and novel laser scanner flaw detection system having smaller spot size and better resolution on wide webs.

Still a further object of this invention is to provide a new and novel laser scanner flaw detection method and system for reducing the system spacing requirements and accordingly requiring smaller areas for the scanner-receiver portion of the system.

Still a further object of this invention is to provide a new and novel wide web laser scanner flaw detection system which ease the problems of severe temperature gradients which prohibits placing the scanner at an extreme position above the web of material being inspected.

Still another object of this invention is to provide a new and novel wide web laser scanner flaw detection system and method which utilizes common electronic processing circuitry alleviating the expense of utilizing a duplication of such circuitry.

In carrying out this invention in one illustrative embodiment thereof, a plurality of laser beams are scanned by a plurality of aligned synchronized rotary scanners on a predetermined scan path over the material being examined with each of the laser beams scanning a portion of the scan line. The rotary scanners are selectively blanked in sequence such that only one rotary scanner is scanning one laser beam on a portion of the scan line of the material at any given time interval. The web of material being inspected is moved in a direction transversely with respect to the scan line for providing a raster type scan pattern of the material being inspected. A receiver having a detector means is positioned for receiving radiation applied from the laser beams from the material with the detectors generating signals in response to the intensity of the radiation received. Electronic processing circuitry is provided to which the detector signals are applied for processing the signals to detect and locate flaws in the material being inspected. In the preferred form of the invention, a single receiver having common electronic processing circuitry is employed. Alternatively, a plurality of receivers, one for each laser scanner may be employed to separately receive radiation from that portion of the material being inspected by each scanner means while the detector outputs therefrom are applied to common electronic processing circuitry.

Advantageously, the method and apparatus in accordance with the present invention reduces the spot size of the laser beam and therefore increases the system resolution. The reduced spacing between the scanners and the material being inspected reduces the volume requirements of the receiver-scanner portion of the system and avoids the problem of severe temperature gradients which would prohibit placing the scanner at extreme locations above the web in a vertical direction. Also, common electronic processing circuitry is employed as well as utilization of a single receiver in the preferred embodiment.

BRIEF DESCRIPTION OF THE DRAWINGS

The invention, together with further objects, aspects and advantages thereof, will be more clearly understood from the following description taken in connection with the accompanying drawings.

DESCRIPTION OF THE PREFERRED EMBODIMENTS

Figure 1:
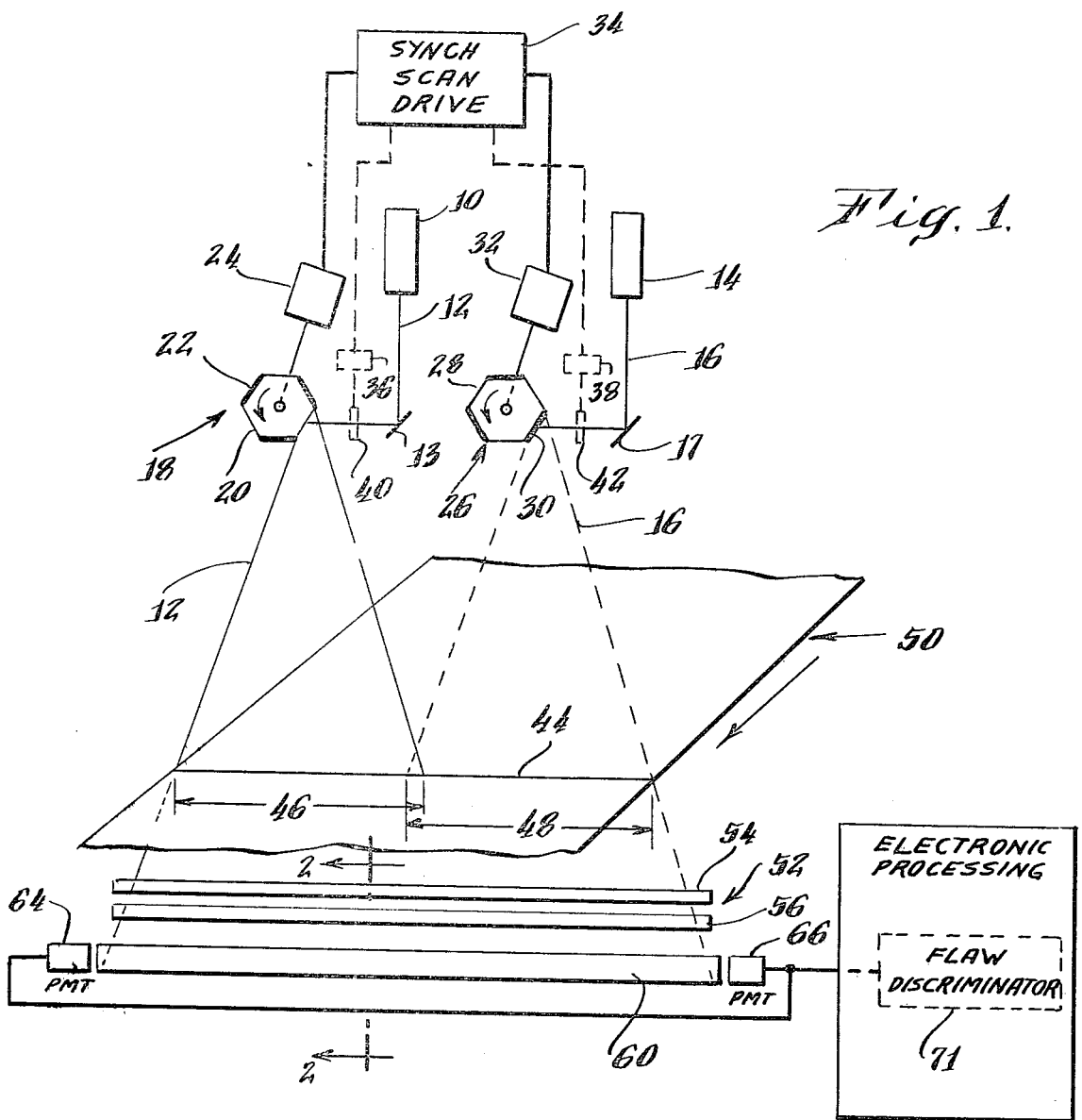
FIG. 1 is a schematic illustration of the wide web laser scanner flaw detection method and system embodied in the present invention.

Referring now to FIG. 1, suitable sources of radiation, for example laser beams 12 and 16 which are generated by lasers 10 and 14, respectively are applied by suitable light forming optics (not shown) via mirrors 13 and 17 to rotary scanners 18 and 26. The folded optical arrangement provided by mirrors 13 and 17 are not required, and the laser beams may be applied directly to the rotary scanners depending upon the spacing between the scanners and the particular application in which they are employed.

The scanners 18 and 26 are conventional multifaceted mirrored surface polygons which are illustrated in FIG. 1 having six facets. It should be appreciated that the rotary scanning drum may have more faces and the more conventional twelve faceted drum is illustrated in connection with the embodiment of FIG. 4. The rotary scanners 18 and 26 are characterized by having alternating mirrored surfaces 20 and 28 alternating with opaque or blanked surfaces 22 and 30, respectively.

The rotary scanners 18 and 26 perform the function to scan the laser beams 12 and 16, respectively consecutively and successfully across a web or sheet of material 50 being inspected which is continuously moving in the direction shown by the arrow on the drawing. The rotary scanners 18 and 26 causes the beams 12 and 16 to scan a scan line 44 across the surface of the material 50 with the line 44 being made up of a portion 46 scanned by the laser beam 12 and a portion 48 scanned by the laser beam 16. Scanning in the orthogonal direction to create a raster type scan is accomplished automatically by the movement of the web of material 50.

In the embodiment shown in FIG. 1 which utilizes two scanners, it is essential that the scanners be synchronized such that when a mirrored surface on scanner 18 is scanning the laser beam 12 across the material on portion 46 that a corresponding opaque surface 30 has the laser beam 16 applied thereto so that the laser beams 16 is prevented from scanning the material at the same time that scanning is taking place by the laser beam 12 and vice-versa which provides a means for locating the cross web position of a flaw on the material being inspected. Such would not be the case, if both scanners were scanning simultaneously. Accordingly, two laser beams 12 and 16 alternate with each scanning a portion of the scan line 44 on each scan across the surface of the material 50. Scanner 18 is driven by a scan motor 24 and scanner 26 is driven by a scan motor 32 which are both coupled to a synchronized scan drive circuit 34 for producing a synchronous scan of the scanners 18 and 26 across the web 50.

As an alternative to the arrangement shown in FIG. 1 in which the facets of the scanners 18 and 26 alternate between mirrored and opaque surfaces, the laser beams 12 and 16 may be alternately blanked from appearing on the scanners by any suitable means such as a shutter or vane 40 and 42 actuated and controlled by a shutter or vane control means 36 and 38 operated from the synchronous drive 34. The shutter or vane controls 36 and 38 may be in any suitable form such as a galvanic movement which opens and closes the shutter or pivots the vane to block or let the laser beam pass.

Figure 2:
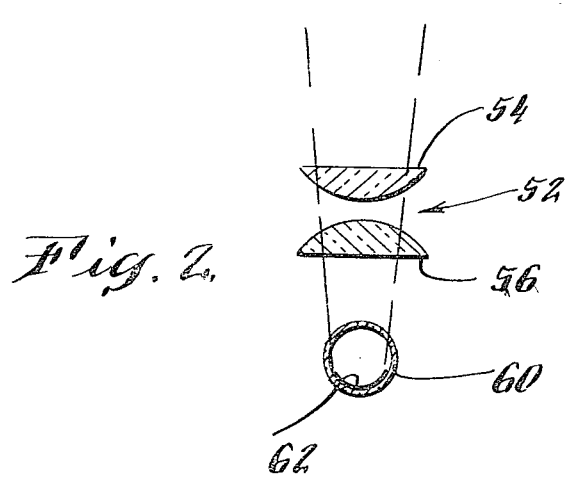
FIG. 2 is a cross-sectional view taken along line 2—2 of FIG. 1 illustrating one type of receiver which may be employed in the present invention.

Light transmitted through the web 50 is applied by an optical means 52 to a receiver 60 which in FIG. 1 comprises a radiation conducting rod. The optical means 52 comprises cylindrical lens 54 and 56 which direct the light from the web 50 to the radiation conducting rod 60 as shown in FIG. 2. The radiation conducting rod 60 has a diffuse strip thereon for dispersing the radiation within the rod to prevent it from passing through the rod or being reflected directly back out of the rod, and the radiation diffused thereby is internally reflected down the rod to suitable detectors 64 and 66 such as photomultiplier tubes which detect the light applied thereto.

Although FIG. 1 illustrates a transmission system in which the receiver 60 collects radiation passing through the web, it should be appreciated that a reflective system may be employed. In the reflected arrangement, the receiver is positioned above the web 50 to receive radiation reflected from the surface of the web 50.

At any instant of time during the scan, the detectors 64 and 66 provide an output which is proportional to the transmission of the spot of light on the material 50 on which the laser beams are impinging. Flaws occurring in the material 50 being inspected change the output of the detectors due to the transmissive properties of the material thereby providing a means for indicating flaws in the material 50. Signals from the detectors 64 and 66 are fed to electronic processing circuitry 70 which may include one or more flaw discriminators 71 for detecting and further processing flaws in the material.

The electronic processing circuitry 70 may provide a number of functions such, for example as sorting and routing the flaws depending upon their location in the material 50, counting the flaws, selectively counting the flaws such that the same flaw is counted again on subsequent scans of the same flaw, etc. Some of these functions are shown and described in U.S. Pat. Nos. 3,900,265 and 3,980,891 which have been previously cited.

In accordance with the embodiment shown in FIG. 1, two scanners are employed which use a common receiver as well as the same electronic processing circuitry. If one scanner was used in place of the two illustrated, it would have to be positioned at a height above the web 50 double that of the height required for the embodiment using two scanners illustrated in FIG. 1. Accordingly, smaller spot size and an increased resolution are obtained when total scan time per line is the same with only the addition to an additional scanner and synchronizing circuitry for synchronously driving the two scanners.

Figure 3:
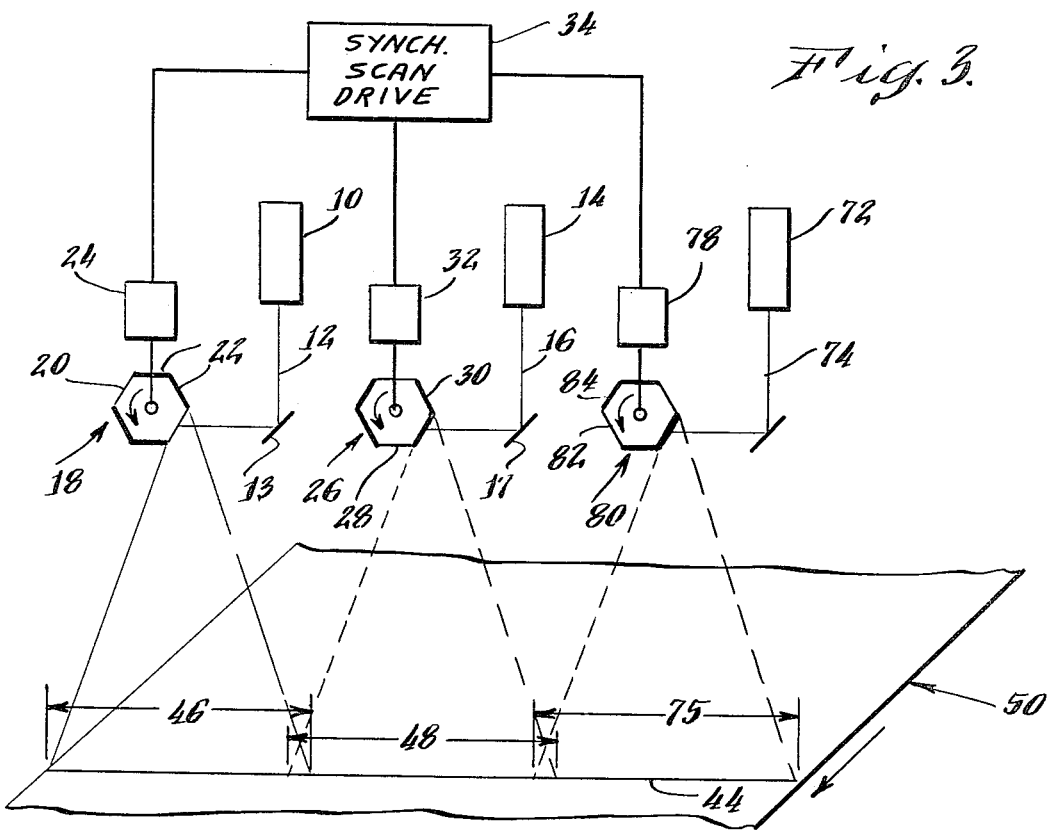
FIG. 3 is a schematic diagram illustrating the use of three rotary scanners and multiple receivers in accordance with further aspects of this invention.

The use of a plurality of scanners to cover wide web materials is not restricted to the use of two scanners as illustrated in FIG. 1 and may include three or four scanners. FIG. 3 illustrates the use of three scanners with the addition of scanner 80 driven by scanning motor 78 which scans a laser beam 74 from a laser 72 across scan line portion 75 of the scan line 44 along the web 50. Again the scanners 18, 26 and 80 must be synchronized so that only one mirrored facet of each scanner is scanning across the web in any given time interval with the accumulated result being one complete scan line 44 made up of the scan portions 46, 48 and 75 traced by the laser beams 12, 16 and 74, respectively by their respective scanners. To accomplish this result it will be noted that each scanner is provided with only two mirrored surfaces and four opaque surfaces in the configuration shown in FIG. 3.

FIG. 3 also illustrates the use of multiple receivers 85 illustrated as three in number, one for each scanner. Each receiver is provided with a detector 86 such as a photomultiplier tube whose outputs are applied to common electronic processing circuitry 70. The receivers 85 may be of the type illustrated and described in U.S. Pat. No. 3,900,265 or they may consist of three radiation conducting rods each having detectors whose outputs are applied to the electronic processing circuitry 70.

By increasing the number of scanners, the height above the scanner for a wide web is again reduced as compared to the single or two scanner arrangements. The reduction of the scanner-web separation is inversely proportional to the number of scanners employed. This reduction in height between the scanner and the web again reduces spot size and increases the system resolution. Although FIG. 3 illustrates the use of a plurality of receivers, a single receiver may be employed in this embodiment.

Figure 4:
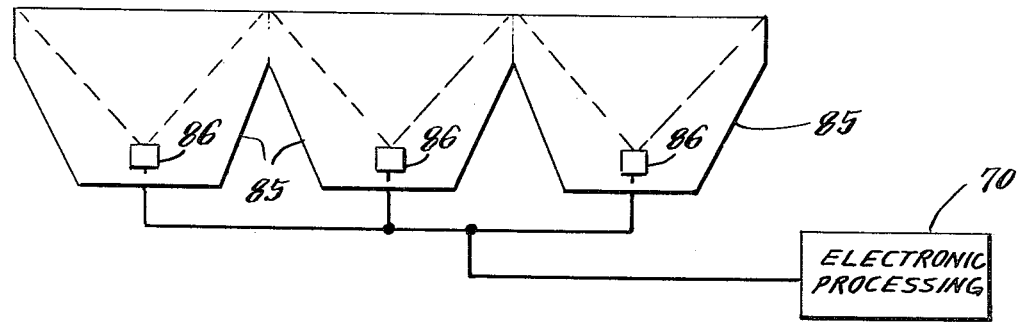
FIG. 4 illustrates the use of a multifaceted mirrored drum for scanning the laser beam across the web of material being examined which has more facets than the scanners previously illustrated and which are shown modified or blanked in accordance with the present invention.
Figure 4:
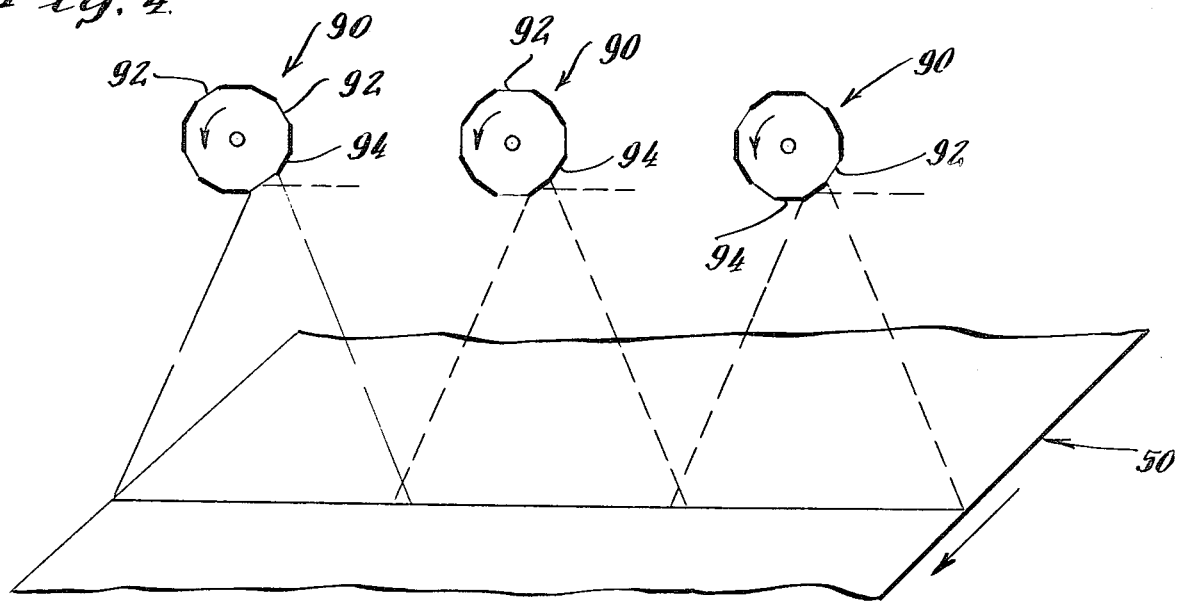

FIG. 4 illustrates the use of the more conventional twelve facet mirrored scanning drum 90 which is currently used in rotary scanner laser flaw inspection systems. The scanners 90, when three scanners are employed, have mirrored surfaces 92 alternating between two opaque facets 94 thereby providing a total of four mirrored facets and eight opaque facets. In an application requiring four scanners, each twelve faceted scanner would have three mirrored surfaces which alternate between three consecutive opaque surfaces. As in the other embodiments the scanners 90 must be synchronized so that only one mirrored surface is scanning a laser beam across the material 50 in any given time interval. Accordingly, when one facet completes scanning its associated laser beams, the next scanner takes over having a mirrored surface which scans the next laser beam across the next portion of the web while the other two have the laser beams blocked by opaque facets. When the third scanner takes over with its mirrored facets scanning the laser beam across the material, the other two laser beams are blanked out again by opaque facets on the other scanners. Accordingly, as before, the scanners 90 must be synchronized in order to achieve the scanning result of cooperatively scanning a complete line across the web 50.

In the illustrated embodiments, it should be observed that the most expensive piece of equipment of the laser inspection system namely the processing electronics may be used with the plurality of scanners. Also a single receiver means may also be used but even if a plurality of receivers are used, the same electronic processing console will be employed saving space and expense. By employing a plurality of scanners, the laser scanner flaw detection systems can be applied to the inspection of very wide webs.

Since other changes and modifications varied to fit particular operating requirements and environments will be apparent to those skilled in the art, the invention is not considered limited to the examples chosen for purposes of illustration, and covers all changes and modifications which do not constitute a departure from the true spirit and scope of this invention.

What is claimed is:

1. A wide web laser scanner flaw detection system for inspection of wide web materials comprising:
   (a) a plurality of lasers for emitting a plurality of laser beams,
   (b) a plurality of aligned synchronized rotary scanner means for repetitively scanning said sources in sequence in a predetermined scan path over the material being examined, each of said laser beams scanning a portion of a scan line,
   (c) said rotary scanner means being selectively blanked in sequence such that only one rotary scanner is scanning a laser beam on a portion of a line scan on said material in any given time interval,
   (d) said blanking being staggered on said plurality of rotary scanner means such that one complete scan line is formed across the material by consecutive sequential alternating scans of each of said laser beams by each of said rotary scanning means,
   (e) means for moving said web in a direction transversely with respect to said scan line for providing a raster type scan pattern of said material being inspected,
   (f) receiver means having detector means positioned for receiving radiation applied by said laser beams from the material being inspected,
   (g) said detector means generating signals in response to the intensity of radiation from said laser beams applied thereto from the material being inspected, and
   (h) electronic processing means having said detector signals applied thereto for processing said signals to detect and locate flaws in the material being inspected.

2. The wide web laser scanner flaw detection system set forth in claim 1 in which a single receiver means is employed.

3. The wide web laser scanner flaw detection system set forth in claim 1 or 2 wherein said receiver means comprises a radiation conducting rod with said detector means positioned on the ends thereon to detect the radiation transmitted thereto by internal reflection along said rod.

4. The wide web laser scanner flaw detection system set forth in claim 1 in which said receiver means comprises a plurality of receivers, one for each laser scanner means positioned to separately receive radiation from that portion of the material being inspected by each scanner means, and means for coupling the detector output of each of said receivers to a single electronic processing means.

5. The wide web laser scanner flaw detection system set forth in claim 1 or 2 in which said plurality of rotary scanner means comprises a drum having a plurality of multifaceted, mirrored surfaces thereon, said surfaces being selectively blanked by having a non-reflective surfaces thereon.

6. The method of inspecting wide webs of material for the detection of flaws by scanning the material with radiation and detecting changes in radiation from said web for delineating flaws therein comprising the steps of:

moving the wide web of material past a plurality of radiation sources, repetitively and selectively scanning each of said radiation sources sequentially and transversely with respect to the direction of movement of said web, each source being scanned on a predetermined portion across said web such that collectively said plurality of sources scan a complete line across said web thereby collectively generating a raster type scan pattern across said web, collecting radiation from said plurality of radiation sources from said web using a single receiver, detecting the radiation gathered by said single receiver, and processing said detected radiation from said plurality of radiation sources using common processing circuitry.

7. The method of inspecting wide webs of material set forth in claim 6 in which said step of selectively scanning each of said radiation sources sequentially across said web includes sequentially blanking said sources thereby preventing more than one source from scanning said web at the same time.

* * * * *